United States Patent [19]

Boström et al.

[11] Patent Number: 5,728,148
[45] Date of Patent: Mar. 17, 1998

[54] STYLET UNIT FOR IMPLANTING A MEDICAL ELECTRODE CABLE

[75] Inventors: Mats Boström, Sundbyberg; Johan Ryden, Solna, both of Sweden

[73] Assignee: Pacesetter AB, Solna, Sweden

[21] Appl. No.: 747,156

[22] Filed: Nov. 8, 1996

[30] Foreign Application Priority Data

Nov. 8, 1995 [SE] Sweden ................................ 9503949
Apr. 23, 1996 [SE] Sweden ................................ 9601541

[51] Int. Cl.$^6$ ................................................. A61N 1/05
[52] U.S. Cl. ................ 607/116; 607/122; 128/642; 128/772; 604/264
[58] Field of Search ................................ 607/116, 122; 128/642, 772; 604/280, 282, 264

[56] References Cited

U.S. PATENT DOCUMENTS

| | | |
|---|---|---|
| 4,136,703 | 1/1979 | Wittkampf . |
| 4,790,331 | 12/1988 | Okada et al. . |
| 4,867,174 | 9/1989 | Skribiski . |
| 5,170,787 | 12/1992 | Lindegren . |
| 5,267,982 | 12/1993 | Sylvanowicz . |
| 5,364,376 | 11/1994 | Horzewski et al. . |

FOREIGN PATENT DOCUMENTS 664 287  2/1988  Switzerland .

*Primary Examiner*—Jennifer Bahr
*Assistant Examiner*—David Ruddy
*Attorney, Agent, or Firm*—Hill, Steadman & Simpson

[57] ABSTRACT

A stylet unit suitable for stiffening a hollow electrode cable, such as during the introduction and the anchoring of a medical electrode cable in the human body, includes a combination of a pair of flexible, coaxially arranged stylet elements, i.e., a tubular stylet sleeve and an internal stylet, which can be inserted into a channel in the sleeve and whose end section is pre-bent to one side. Both the stylet sleeve channel and moving inner stylet contained therein have sections or segments with non-circular cross-sections, the profile of the stylet's non-circular cross-section, in relation to the profile of the sleeve channel's non-circular cross-section, preventing the stylet from rotating in relation to the surrounding sleeve, at least within the parts of the sleeve in which both the stylet and the sleeve channel have interacting non-circular cross-sections. The stylet sleeve also has a distal end section which is pre-bent in a first lateral direction in relation to the stylet unit, and the inner stylet's distal end section is pre-bent in the diametrically opposite lateral direction. The rotation-preventing non-circular cross-sections ensure that the oppositely pre-bent stylet and sleeve portions remain in the same plane, so the forces respectively produced by each substantially cancel, thereby facilitating relative movement of the stylet in the sleeve.

20 Claims, 5 Drawing Sheets

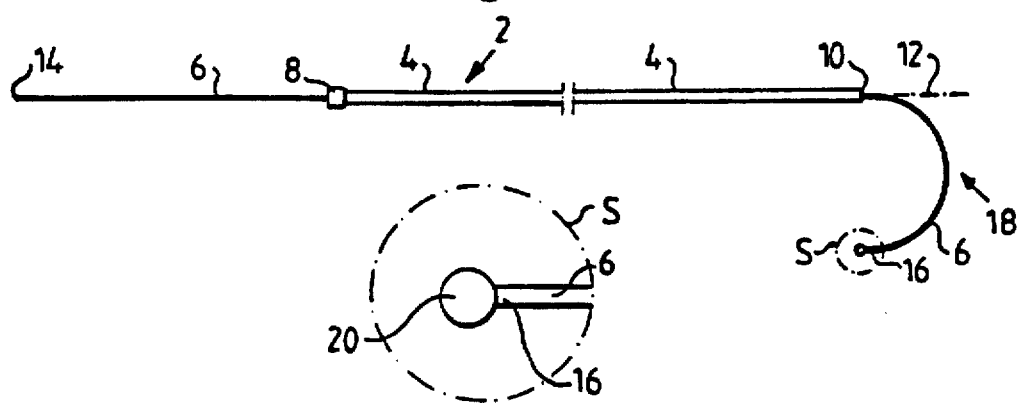
Fig. 1
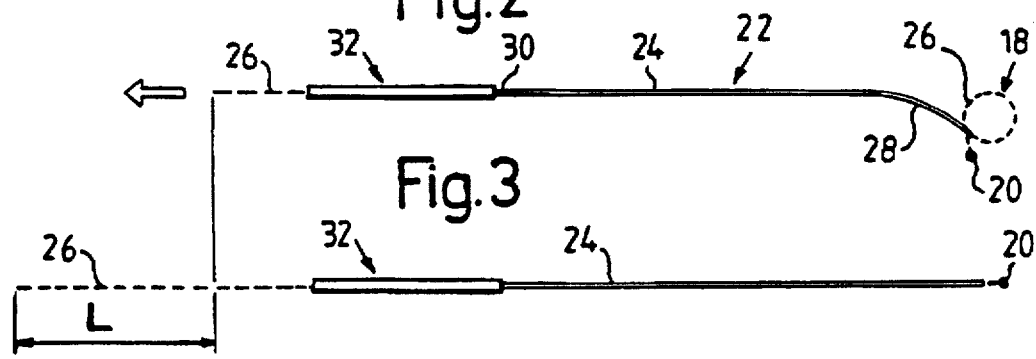
Fig. 2
Fig. 3
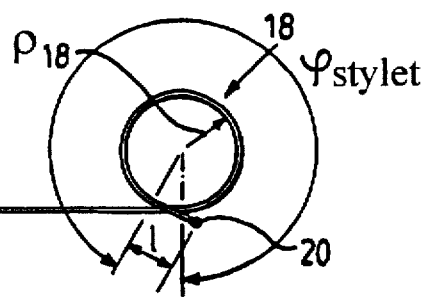
Fig. 4
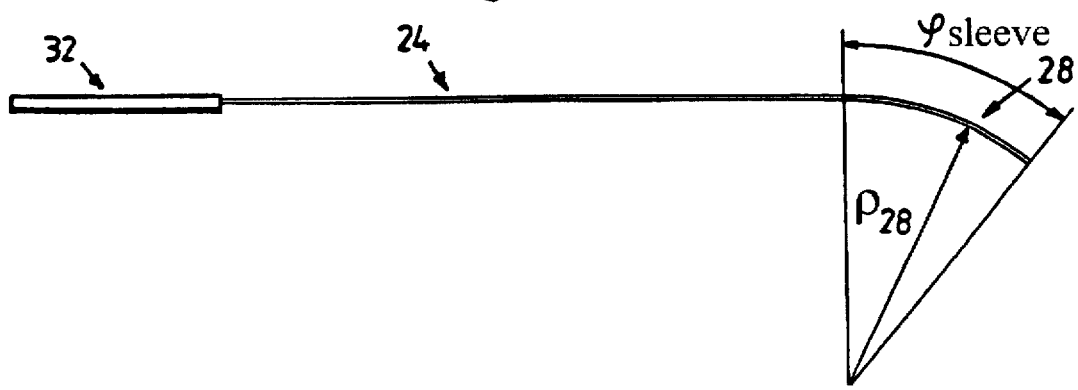
Fig. 5

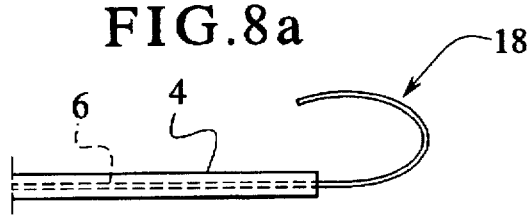
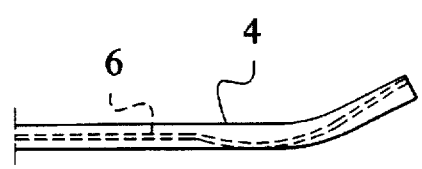
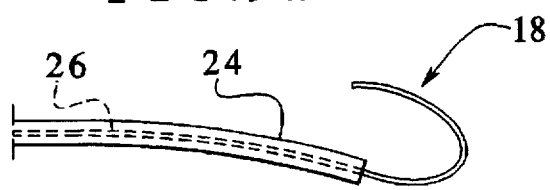
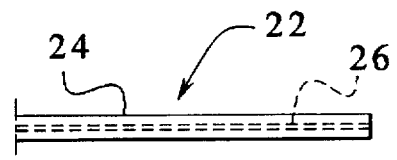
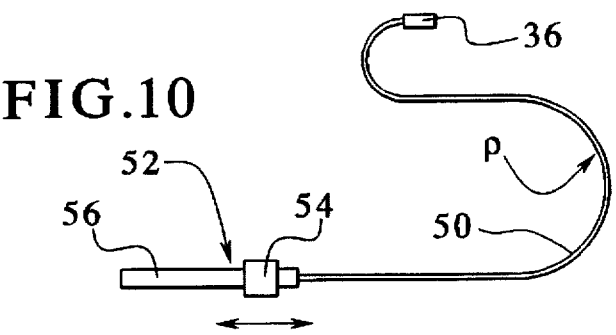
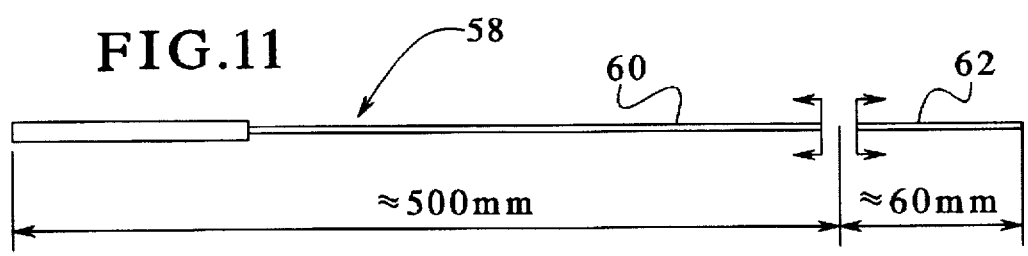
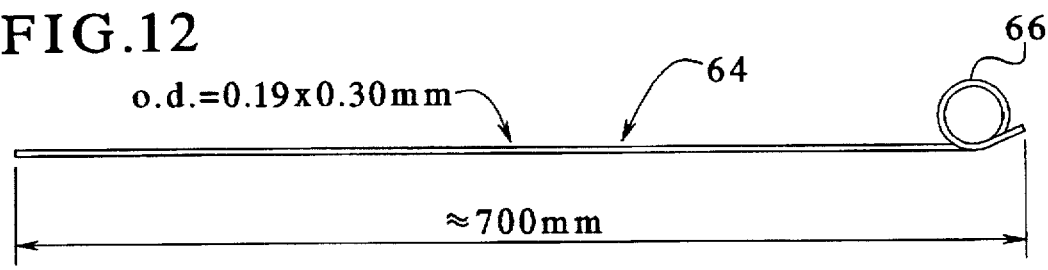

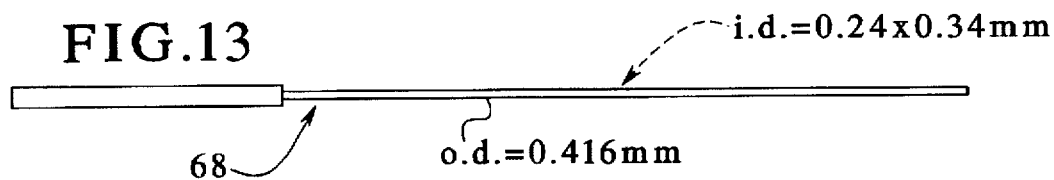
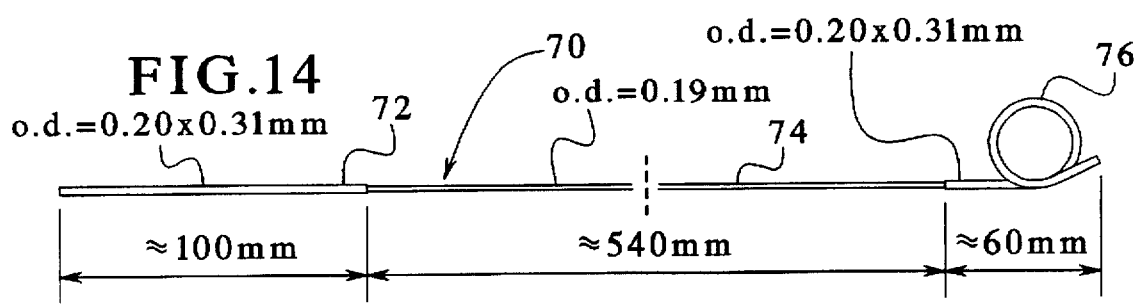
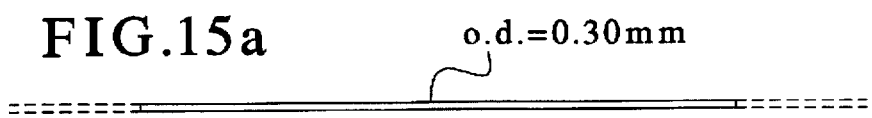
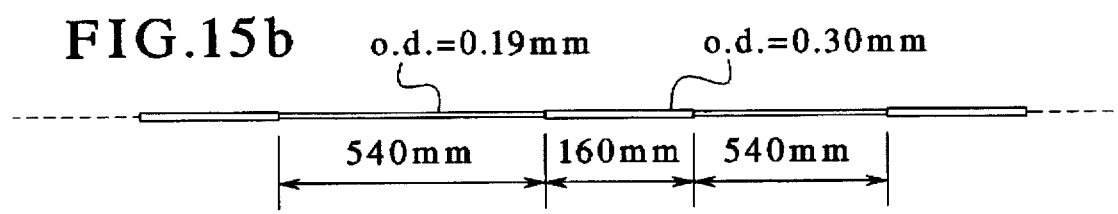
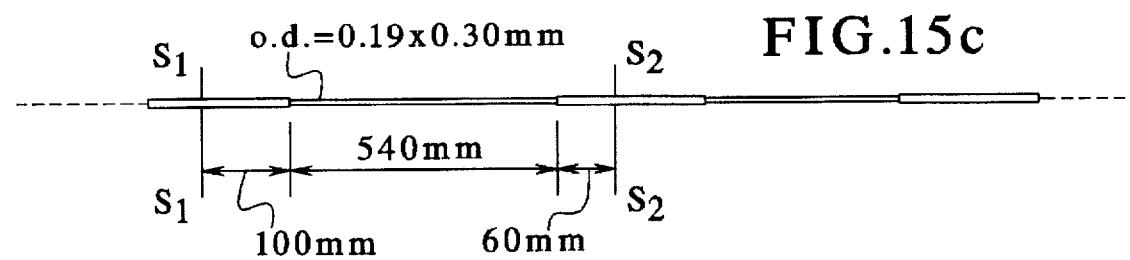
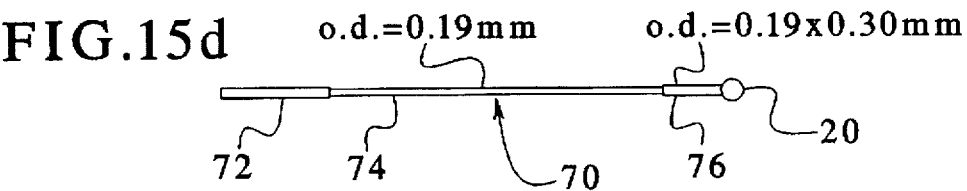

STYLET UNIT FOR IMPLANTING A MEDICAL ELECTRODE CABLE

BACKGROUND OF THE INVENTION

1. Field of the Invention

The present invention relates to a stylet unit, which can be inserted into an elongate means with an internal longitudinal channel, such as an electrode cable for a heart stimulator, a coronary catheter or some other kind of hollow, oblong instrument, in order to stiffen the elongate means and to bend a distal end section thereof, the stylet unit including a flexible, tubular stylet sleeve and an inner stylet, which can be inserted into the sleeve, channel, with a distal end section pre-bent to one side.

An elongate channel-equipped means of the aforementioned kind can e.g. be a tubular conductor used for achieving stimulation inside the human body. The channel-equipped means can either serve as the implant or be removed from the body after treatment is concluded.

2. Description of the Prior Art

A stylet unit of the above general type is especially suitable for stiffening and maneuvering a hollow electrode cable for a heart stimulator, in conjunction with introduction of the electrode cable into a patient's heart, and for anchoring the contact electrode (electrode head) on the distal end of the cable in a cavity in the heart. 'Introduction of such an electrode cable into the heart is usually performed through a suitable vein, and the contact electrode can be anchored in the right ventricle or atrium. The stylet unit temporarily contained inside the hollow electrode cable extends through the cable's central channel from the cable's proximal end (which is subsequently connected to the heart stimulator) to its distal end on which the contact electrode is located.

Especially in the anchoring of a contact electrode in the heart's atrium, a stylet unit is appropriately used with which the distal end section of the electrode cable can be given a suitable I shape, simplifying introduction of the end section into the atrial auricle and anchoring of the contact electrode in the trabeculae of the atrial auricle. After the contact electrode has been anchored at the desired site in the heart, the stylet is withdrawn from the electrode cable.

U.S. Pat. No. 5,170,787 describes and shows (see FIG. 2 in the patent document) a stylet unit with a double stylet combination consisting of a flexible, tubular stylet sleeve holding an inner stylet which is moveable in the sleeve's central channel. At the proximal end of this known stylet unit, there is an operating handle with which the sleeve and inner stylet can be moved in relation to each other to retract the stylet's pre-bent distal end section into the distal end section of the surrounding sleeve, or to deploy the pre-bent distal end section outside the opening of the sleeve's end section into the central channel of the distal end section of the surrounding electrode cable, thereby imparting the desired bent shape to the end of the cable.

U.S. Pat. No. 4,136,703 describes and shows another example of a stylet unit, devised as a double stylet combination, for an electrode cable, containing an inner stylet with a pre-bent distal end section. These known types of stylet units, devised as double stylet combinations, do not ensure that the stylet unit (and, accordingly, the surrounding electrode cable) is completely straight when the inner stylet's pre-bent distal end section is fully retracted inside the stylet sleeve.

SUMMARY OF THE INVENTION

An object of the present invention is to provide a stylet unit devised to form a completely straight double stylet combination when the inner stylet (whose distal end section is pre-bent to one side) has been retracted into the stylet sleeve to an extent that the distal end section of the stylet is also inside the stylet sleeve. When this pre-bent end section is deployed outside the opening of the stylet sleeve, it bends the corresponding section of the surrounding channel-equipped means which (as noted above) can be a hollow cable, a catheter or some other elongate instrument displaying flexural stiffness.

Another object of the present invention is to provide a stylet unit in which the stylet sleeve channel and the moving inner stylet therein are devised so the stylet is kept from rotating in relation to the surrounding sleeve within at least a longitudinal section and/or in the area of at least a local section of the sleeve channel, at least at a given axial position for the stylet in relation to the stylet sleeve.

An additional object of the present invention is to provide a stylet unit which is designed so the structure which prevents undesirable rotation of the stylet in relation to the surrounding stylet sleeve do not cause excessively high contact pressure and, accordingly, does not produce a operating force which increases friction between the stylet and the interior of the sleeve channel.

Another object is to provide a stylet unit which is devised so that two or more longitudinal sections of the stylet inside the stylet sleeve's central channel are prevented from rotating in relation to the stylet sleeve, thereby making the stylet unit reliably maneuverable from the unit's proximal end.

Yet another object is to provide a stylet unit which displays a very pronounced J shape when the inner stylet's distal end section has been fully deployed outside the opening of the stylet sleeve.

The above object is achieved in accordance with the principles of the present invention in a stylet unit insertable into a channel in an elongated element, such as a medical electrode cable, the stylet unit including a double stylet combination formed by a flexible, tubular stylet sleeve and an inner stylet insertable into a channel in the stylet sleeve. The stylet has a distal end section which is pre-bent in a plane, and the stylet sleeve and the stylet each have at least one longitudinal section with a non-circular cross-section, the non-circular cross-sections of the sleeve and the stylet being matched in shape so as to prevent rotation of the stylet in the channel of the sleeve.

Thus, the most distinctive feature of the stylet unit according to the invention is that the stylet sleeve has at least one longitudinal section or segment within which the sleeve channel has a non-circular cross-section, and the inner stylet, which can move inside the stylet sleeve, has at least one longitudinal section with a non-circular cross-section, and the profile of the stylet's non-circular cross-section, in relation to the profile of the sleeve's non-circular channel cross-section, so that the stylet is prevented from rotating in relation to the surrounding sleeve in the areas of the sleeve in which the stylet and the stylet channel have interacting non-circular cross-sections.

Within the scope of the invention in its aforementioned general form, a number of different combinations of interacting parts and/or areas with non-circular cross-sections for the stylet sleeve channel and the stylet insertable into same are also possible.

The stylet sleeve, for example, could have a first longitudinal section in which the channel has a circular cross-section and a subsequent, second longitudinal section in which the channel has a non-circular cross-section, with the inner moving stylet, which can be inserted into the stylet sleeve, having a non-circular cross-section for most of its length. In an alternative embodiment, the stylet sleeve channel can have a non-circular cross-section over most of the length of the sleeve, while the inner stylet has a first longitudinal section with a non-circular cross-section, a subsequent second longitudinal section with a circular cross-section and, finally, a third longitudinal section with a non-circular cross-section.

From the manufacturing point of view, however, it would be preferable for both the stylet channel and the moveable inner stylet to have a non-circular cross-section over most of their lengths, preventing the stylet from rotating, in relation to the surrounding sleeve, over all of its length.

The stylet sleeve can appropriately have a distal end section which is pre-bent in a first lateral direction in relation to the stylet unit, whereas the distal end section of the inner stylet is pre-bent in the diametrically opposite direction.

In other words, it is important for both the stylet and surrounding stylet sleeve channel to have the same interacting non-circular cross-sectional shape, at least within one or more interacting segments, areas or sections. The respective pre-bent end sections of the stylet and sleeve are then preferably located on the same plane on which the midline of the stylet sleeve channel is also located.

A stylet unit constructed in accordance with the principles of the present invention ensures that the outward, lateral bending of the stylet sleeve, caused by the inner stylet's pre-bent distal end section when retracted into the sleeve, is compensated for and cancelled by the lateral outward bending, produced by the stylet sleeve's own pre-bent distal end section, in the diametrically opposite direction. In this manner, the stylet unit can be made to display a straight distal end section when the end section of the inner stylet is fully retracted into the end section of the sleeve.

To ensure that both lateral outward bends (i.e. the bend of the inner stylet and the sleeve's own preset outward bend) are in the same plane, thereby completely canceling out each other, there must be no internal rotation between the inner stylet and surrounding sleeve in the bent area. Any such rotation between the stylet and sleeve would cause the pre-bent distal end section of the inner stylet to produce uncontrolled lateral outward bending or unpredictable bending of the surrounding sleeve. The respective interacting, non-circular cross-sections of the stylet and sleeve according to the invention prevent any such uncontrolled bending and ensure "stable" interaction between because the stylet automatically assumes a stable position corresponding to its lowest energy state.

Each of the distal end section of the stylet sleeve and the distal end section of the stylet are appropriately pre-bent with an approximately constant bending radius, the stylet's bending radius, however, being much smaller than the sleeve's bending radius. The sleeve's pre-bent end section can appropriately cover an angle less than 90°, preferably not more than 45°. The stylet's pre-bent end section can have a curve length corresponding to a complete bending turn, causing the pre-bent end section to assume the shape of a closed loop.

With an appropriate choice of curvature radii, curve lengths and flexural stiffnesses for the respective pre-bent end sections of the stylet and, the stylet unit can be kept completely straight when the stylet's pre-bent end section is completely retracted into the sleeve's distal end section.

One of the inherent difficulties, especially when a stylet unit for medical purposes is involved, is to master the special construction and strength problems posed by the very small dimensions of the inner stylet and its surrounding stylet sleeve and the dimensional relationship of the stylet/sleeve respectively.

The stylet unit's dimensions and flexibility are governed by the flexibility needed for the unit to be able to follow the physiological and anatomical limitations encountered during the introduction of an electrode cable or catheter into the human body, but the diameter of the inner stylet must not be too small, and the stylet (with its exposed, pre-bent distal end section) must still be capable of bending the hollow cable or catheter in which it is enclosed. A stylet diameter, for example, on the order of 0.20–0.25 mm with an external sleeve diameter, for example, on the order of 0.30–0.45 m are appropriate for the inner stylet and associated stylet sleeve (i.e. a stylet unit designed for an electrode cable).

The inner stylet's non-circular profile is appropriately the same as the corresponding, interacting non-circulating cross-sectional profile of the stylet channel, and the play, or tolerance, between these interacting components should appropriately amount to at least 0.02 mm to ensure that relative movement between the inner stylet and the surrounding sleeve can take place without problem and with reasonable friction resistance.

A number of different non-circular cross-sectional profiles are possible for the respective interacting sections, areas or segments of the inner stylet and sleeve channel. Oval, elliptical or polygonal shapes, preferably with somewhat rounded corners, are examples.

With a stylet unit according to the invention, the distal end section of the stylet unit can be made to display e.g. a U-shaped or J-shaped bend when the stylet's pre-bent end section is fully deployed outside the stylet sleeve's corresponding distal end section.

The invention also includes an elongate, tubular means such as a hollow electrode cable with an interior stylet unit of the kind cited above. When the stylet unit has been inserted as far as possible into the electrode cable's channel and the inner stylet's distal end section is exposed and deployed outside the stylet sleeve's distal end section, the bent distal end section of the electrode cable plus the straight part of the cable assume a fish hook-like J shape. The electrode cable's distal end section is equipped with a contact electrode running substantially parallel to the straight part of the cable towards the cable's proximal end, which is designed for connection to a heart stimulator or pacemaker after the electrode cable has been introduced into a patient's heart, and the contact electrode has been anchored in a cavity of the heart and the stylet unit has been withdrawn from the electrode cable.

DESCRIPTION OF THE DRAWINGS

FIG. 1 shows a schematic view of a known double stylet combination intended for stiffening and bending an electrode cable (not shown).

FIG. 2 shows a first embodiment of a stylet unit according to the invention with a pre-bent distal end section which has not yet been retracted into the stylet sleeve.

FIG. 3 shows a stylet unit according to FIG. 2 with a stylet end section retracted into the stylet sleeve.

FIG. 4 shows the stylet unit's inner stylet according to FIGS. 2–3.

FIG. 5 shows the stylet unit's stylet sleeve according to FIGS. 2–3.

FIGS. 8a and 8b respectively show an end section of a known stylet unit with the inner stylet unit's pre-bent end section in the deployed, exposed position and in the retracted position, inside the sleeve.

FIGS. 9a and 9b respectively show the distal end section of a stylet unit according to the invention with the pre-bent distal end section of the inner stylet in the deployed, exposed position and in the retracted position inside the sleeve.

FIG. 10 is a schematic view showing the way an electrode cable, with an inserted stylet unit may bend while being advanced to a patient's heart.

FIG. 11 shows an example of a stylet sleeve of a second embodiment of a stylet unit according to the invention.

FIG. 12 shows an inner stylet designed to be movable arranged inside the stylet sleeve shown in FIG. 11.

FIG. 13 shows an example of a stylet sleeve of a third embodiment of a stylet unit according to the invention.

FIG. 14 shows an inner stylet designed to be movably arranged inside the stylet sleeve shown in FIG. 13.

FIG. 15a schematically depicts a first stage in the fabrication of a stylet of the kind shown in FIG. 14.

FIG. 15b depicts a second stage in the fabrication of the stylet according to FIG. 14.

FIG. 15c depicts a third stage in the fabrication of a stylet according to FIG. 14.

FIG. 15d depicts a fourth and final stage in the fabrication of a stylet according to FIG. 14.

DESCRIPTION OF THE PREFERRED EMBODIMENTS

Figure 6:
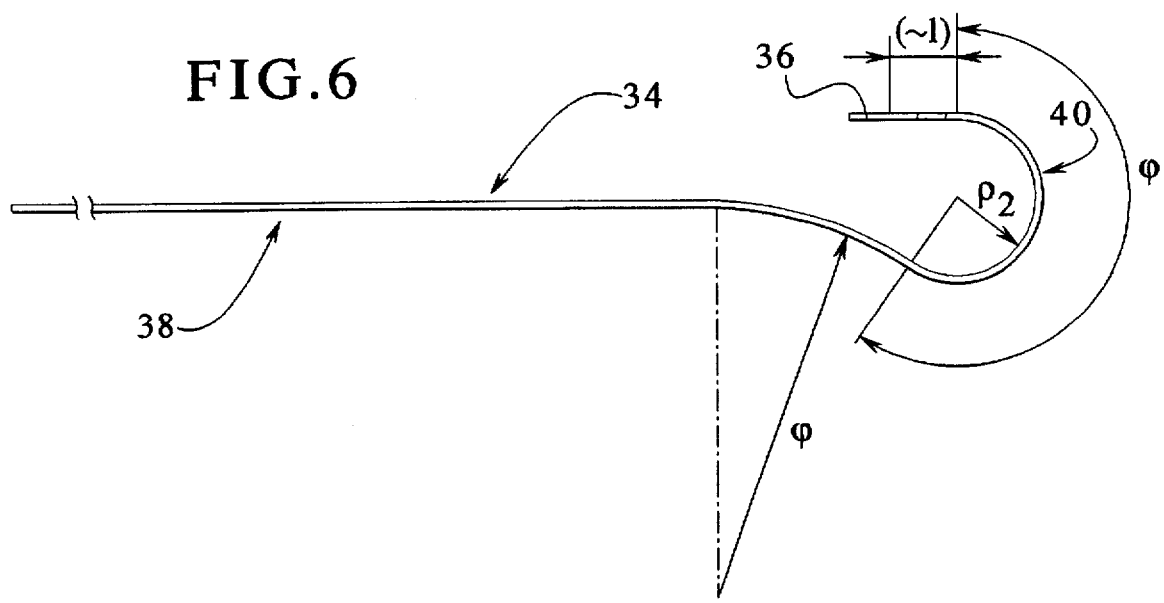
FIG. 6 shows a hollow electrode cable with an inserted stylet unit with a distal stylet end section deployed outside the stylet sleeve.

FIG. 1 schematically shows a known stylet unit 2 which is a double stylet design consisting of a flexible, tubular stylet sleeve 4 and an inner stylet 6 arranged to move freely inside the channel in the sleeve 4. The stylet sleeve 4 has a proximal end 8 and a distal end 10, and the stylet 6, which has a proximal end 14 and a distal end 16, can be moved back and forth inside the sleeve 4 in the axial direction 12 of the sleeve 4. Relative movement between the tubular sleeve 4 and the inner stylet 6 is usually achieved with a manipulation and holder (not shown) at the proximal end 8 of the sleeve 4. Here, a holder could be attached to the stylet sleeve 4, and a gripping element (handle) could be attached to the stylet 6, making it possible to move the stylet in relation to the sleeve when the holder is kept stationary.

The relative movement of the inner stylet and the surrounding sleeve could, of course, also be achieved by keeping the stylet 6 stationary and moving the sleeve 4.

In the area preceding its distal end 16, the inner stylet 6 has a pre-bent distal end section 18 shaped like a semicircle. The distal end 16 of the stylet 6 is also equipped with a small end ball 20 (see the magnified view in the circle S), whose diameter is somewhat larger than the diameter of the stylet sleeve 4 channel, to keep the distal end 16 of the stylet 6 from being inadvertently retracted into the sleeve 4. The risk of penetration of the surrounding electrode cable wall by the stylet is also minimized thereby.

As a result of the relative movement of the stylet 6 and sleeve 4, the stylet's pre-bent end section 18 can either be fully retracted into the sleeve 4 or deployed more or less in the position shown in the FIG. 1, at which the entire distal end section 18 of the stylet 6 projects beyond the distal end 10 of the sleeve 4.

When the stylet unit is a conventional double stylet combination, in which both the stylet 6 and the channel of the sleeve 4 have a circular cross-section, retraction of the pre-bent distal end section 18 of the stylet 6 into the straight stylet sleeve 4 (see FIG. 8a) causes the corresponding end section of the sleeve 4 to bend outwardly to one side (see FIG. 8b) because of the pre-tensioning force arising in the sleeve (when the stylet is retracted into the sleeve), thereby forcing the stylet end section 18 to straighten.

FIGS. 2–3 show a first embodiment of a controllable double stylet unit 22, according to the invention, which has a flexible, tubular stylet sleeve 24 and an inner stylet 26 movingly arranged inside the sleeve channel. The stylet sleeve 24 has a distal end section or segment 28 and a proximal end section 30. The end section 30 is attached to a support tube 32 which makes possible coaxial movement of the stylet 26 and sleeve 24. The parts of the internal stylet 26 which protrude out of the pre-bent end section 28 of the sleeve 14, and out of the end of the holder tube 32, facing away from the end section 30, have been indicated with a dashed outline for clarity. As FIG. 2 shows, the inner stylet 26 has a straight proximal end section outside the support tube 32 and a distal end section 18, forming a circular loop 18, outside the opening of the sleeve end section 28. At the tip of its pre-bent end section 18, the stylet 26 has a small end element in the form of a stop ball 20, which prevents inadvertent retraction of the pre-bent end section 18 too far into the end section 28 of the sleeve 24 as well as preventing penetration of the surrounding electrode cable wall by the end of the stylet 26.

Thus, FIG. 2 shows the stylet unit 22 with the stylet end sections 28 protruding out of the sleeve 24. FIG. 3 shows the stylet unit 22 after the stylet 26 has been axially retracted the stroke distance L out of the support tube 32 and sleeve 24. The circular, pre-bent end section 18 of the stylet 26 has accordingly been fully retracted into the end section of the sleeve 28 so the end stop ball 20 is at the opening of the end section 28. In practice, retraction of the end section 18 into the sleeve section 28 is achieved when the stylet sleeve 24 is slid over the stylet end section 18. Since the distal end section 28 of the sleeve 24 is pre-bent in a direction opposite to the bend of the stylet end section 18, retraction of the stylet end section 18 into the sleeve section 28 causes both pre-bends to cancel each other, enabling the stylet unit 22 to assume the straight configuration shown in FIG. 3. Thus, the "pre-tensioning force", which the stylet end section 18 generates in the sleeve end section 28 when the stylet 26 is retracted into the end section 28, counteracts and cancels the bending of the end section 28 of the sleeve 24 in the opposite direction. For the two bending effects, exerted by the pre-bent end section 28 of the sleeve 24 and the pre-bent end section 18 of the stylet 26, to cancel each other, they must act in opposite directions in the same plane, in this instance in the plane shown in FIG. 2. This requires the inner stylet to be kept from rotating in relation to the surrounding stylet sleeve 24. This rotation-prevention is achieved by providing each of the stylet sleeve 24 and the stylet 26 insertable therein with a non-circular cross-section. In other words, the cross-sectional profile of the stylet 26 must be such that the stylet 26 is incapable of rotating in the channel of the sleeve 24. For the inner stylet 26 to be able to perform the desired coaxial movement inside the stylet sleeve 24, some tolerance or radial play must be left between the cross-sections of the inner stylet 24 and the stylet channel. In practice, it may be appropriate (as noted above in conjunction with examples supplied of values for the diameter of the inner stylet 26 and its associated stylet sleeve 24) for the stylet 26 and sleeve channel to be dimensioned so radial play between them amounts to at least 0.02 mm.

FIGS. 7a, 7b, 7c, 7d and 7e schematically depict some examples of cross-sectional shapes for interacting parts (longitudinal segments, areas or local sections), i.e. the inner stylet 26 plus its surrounding stylet sleeve, the greatly exaggerated play between them being designated δ Both the inner stylet 26 and the surrounding stylet sleeve 24 are appropriately made of metal, preferably steel. Both the stylet, sleeve 24 and the inner stylet 26 are flexible, but the sleeve's moment of inertia (calculated at its surface) is greater than that of the inner stylet 26, due to the prevailing geometry, so retracting the stylet end section 18 into the sleeve's end section 28 has the effect which is apparent upon comparison between FIG. 2 and FIG. 3. The flexural stiffnesses of the sleeve 24 and inner stylet 26 can and should be adapted to the material(s) selected for these stylet unit components. The respective pre-bent end sections of the sleeve 24 and the stylet 26 should therefore have curvature radii, curve lengths and flexural stiffnesses so the straightening, backward bending of the stylet sleeve 24, caused by the stylet 26, and the pre-bending of the sleeve 24 cancel each other when the stylet's pre-bent end section is retracted into the distal end section 28 of the sleeve 24. FIGS. 9a and 9b show schematic and greatly exaggerated views of the way the pre-bending of the stylet 26 and the sleeve 24 is devised to achieve the desired straight configuration for the end section stylet unit 22 end section, as shown in FIG. 9b.

FIGS. 4 and 5 show the shape of the separate inner stylet 26 and the shape of the separate stylet sleeve 24 before the stylet 26 is inserted into the sleeve to achieve the stylet unit 22 configuration shown in FIG. 2. FIG. 4 shows that the distal end section 18 of the inner stylet 26 is pre-bent with a constant bending radius ρ18 which is far smaller than the bending radius ρ28 of the pre-bent end section 28 of the stylet sleeve 24 shown in FIG. 5. Thus, the end section 28 also has a constant bending radius and, in the illustrated instance, a curve length $\phi_{sleeve}$ corresponding to an angle on the order of about 40°. Since the inner stylet's pre-bent end section 18 in FIG. 4 has the shape of a closed loop, the curve length in this instance obviously corresponds to more than 360°.

As FIG. 4 shows, the pre-bent end section 18 of the stylet 26, after a curved length $\phi_{sleeve}$, changes into a straight, concluding end section with the ball 20 attached to its free end. This straight end section has a length 1 whose magnitude is selected with a view to, e.g., current requirements and anatomical conditions in the body cavity in which the bent electrode cable, manipulated by the end section 18, is to be, anchored. The straight end section typically has a length ranging from 5 to 20 mm to facilitate electrode maneuvering, however, much longer stylet end sections can be used in other stylet unit applications.

Figure 7A:
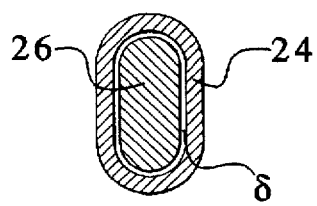
FIGS. 7a, 7b, 7c, 7d and 7e respectively show examples of possible cross-sections of a stylet unit according to the invention.
Figure 7B:
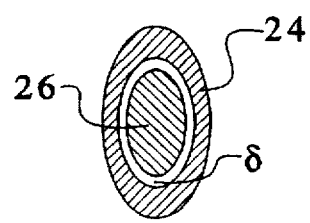
Figure 7E:
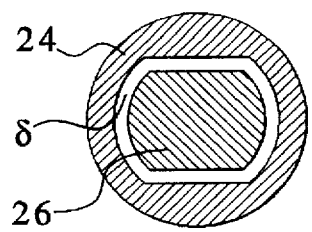
Figure 7C:
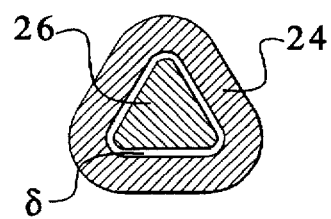
Figure 7D:
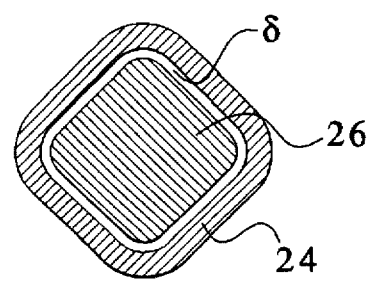

As FIGS. 7a, 7b, 7c and 7d show, the interacting parts or segments of the stylet 26 and sleeve channel with non-circular cross-sections can have identical cross-sections and be devised e.g. as concentric ovals, ellipses or regular polygons with rounded corners. The stylet sleeve 24 can even have a circular-cylindrical exterior, i.e., it can have a completely circular cross-sectional profile for its exterior, as shown in FIG. 7e.

In its fully deployed position outside the sleeve 24, the pre-bent end section 18 of the stylet 26 has the circular loop shape shown in FIGS. 2 and 4, but the curve length of the end section can also be limited to an angle less than 360°, or greater than 360°. It may be suitable in many instances for the distal end section 18 to have a U-shaped or J-shaped bend when the end section 18 is deployed outside the stylet sleeve.

The above-described stylet unit 22 is especially designed for introduction into an electrode cable 34, hollow throughout its length, of the type used with a heart stimulator for transmitting electrical impulses from the heart stimulator to a contact electrode 36, anchored in a cavity of the heart, on the distal end of the electrode cable 34. One example of such an electrode cable 34 with an inserted internal stylet unit 22 is shown in FIG. 6. When the stylet unit 22 is inserted into the electrode cable 34, it is advantageous for the stylet unit 22 to have the straight shape shown in FIG. 3. The stylet unit 22 is inserted into the very flexible and "floppy" electrode cable 34 in order to stiffen the cable 34 during advancement through a suitable vein to the heart. In the introduction into and anchoring of the contact electrode 36 of the cable 34 in e.g. the heart's right atrium, the stylet unit 22 is also used to achieve an appropriate curvature for the end section of the cable 34, where the contact electrode 36 is located. This bending of the end section of the cable 34 is achieved when the shape of the stylet unit 22 is changed from the straight configuration shown in FIG. 3 to the shape in which both the stylet sleeve 24 and the inner stylet 26 have bent end sections, as shown in FIG. 2. Since the electrode cable 34 is much thicker than the distal end section 18 of the stylet 26, the stylet 26 is incapable of bending the electrode cable 34 into a loop, and instead gives the distal end of the electrode cable 34 a fish hook-like shape, as shown in FIG. 6. The distal end section of the cable 34, equipped with the contact electrode 36, then runs essentially parallel to the straight section 38 of the cable 34, toward the proximal end of the cable 34.

Referring to FIGS. 10–15, the stylet unit 22 according to the invention will now be exemplified with several alternative embodiments in which the stylet sleeve channel and the associated inner stylet 26 do not have a non-circular cross-sections along the entire length of the stylet unit 22.

The background of these alternative embodiments is as follows:

In the use of a stylet unit 22 in which both the stylet sleeve channel and its associated, moving inner stylet 26 do not have a non-circular cross-section along the entire length of the stylet unit 22, certain problems can develop because of increased friction between the stylet 26 and stylet sleeve channel, especially in instances in which the entire stylet unit 22 is subjected to extensive bending. When a hollow electrode cable, with an inserted stylet unit 22, is to be introduced into the heart via the venous system, different parts or sections of the electrode cable will be bent to different degrees, as can be seen in the schematic depiction in FIG. 10, which shows an electrode cable 50 with an hand-operated guide 52 for the stylet unit inserted into the electrode cable. The guide 52 is located at the proximal end of the electrode cable 50. Movement of the inner stylet 26 of the stylet unit 22 (not shown here) in relation to its surrounding stylet sleeve 24 is performed by manual movement of a sleeve part 54 of the guide 52 in relation to a tubular part 56 of the guide 52. A practical problem caused by the increased friction occurring in the bending of the cable 50 is that the use of excessive force may be necessary in order to operate the guide 52.

The increase in friction in the stylet unit 22 is because of elevated contact pressure between the stylet 26 and interior of the sleeve channel when the stylet buckles inside the stylet sleeve 24 and because of other friction phenomena. The buckling phenomenon can be avoided, however, by providing the stylet sleeve channel and the stylet 26 with a rotation symmetrical cross-section instead of a non-symmetrical (non-circular) cross-section at the points at which the electrode cable 50 must be bent.

This can be achieved in general when the stylet sleeve channel or the internal stylet have a circular cross-section only in the bent areas. In the first instance, the stylet sleeve channel is devised with a non-circular cross-section only at the location at which compensating must be made for the flexural moment exerted by the stylet on the surrounding stylet sleeve when the stylet is inserted into the sleeve.

FIGS. 11 and 12 show a first alternative embodiment of the sleeve and attendant stylet. The stylet sleeve, generally designated 58, in this instance has a longer first sleeve part 60 and a shorter second sleeve part 62. The sleeve part 60 is a circular, cylindrical tube with a circular cross-sectional profile for both the interior of the tube channel and the exterior of the tube. The sleeve part 62 also has a circular, cylindrical exterior with a circular cross-sectional profile, the channel's cross-sectional profile being non-circular in this instance.

The inner stylet, generally designated 64, for the sleeve 58 according to FIG. 11 is equipped with a circular, pre-bent distal end section 66 of about the same type shown in FIG. 4. In this instance, the stylet 64 has a non-circular cross-section with the dimensions 0.19 mm×0.30 mm.

FIG. 13–14 show alternative embodiments of a stylet sleeve with an attendant inner stylet in an alternative stylet unit according to the invention.

In this instance, the stylet sleeve, generally designated 68, as shown in FIG. 13, is an externally circular, cylindrical tube but whose internal channel has a non-circular cross-section. Here, the diameter of the sleeve 68 is 0.416 mm, whereas the non-circular cross-section of the sleeve's internal channel is envisaged as being 0.24 mm ×0.34 mm.

The inner stylet, generally designated 70, for the stylet sleeve, generally designated 68, according to FIG. 13 and shown in FIG. 14, in this instance has a shorter first stylet section 72 with a non-circular cross-section, a longer second stylet section 74 with a circular cross-section and a pre-bent, distal end section 76 with a non-circular cross-section. In this instance, the stylet sections 72 and 76 are as both 0.20 mm×0.31 mm, whereas the stylet section 74 is circular and cylindrical with a 0.19 mm cross-sectional diameter.

A stylet 70 of the kind shown in FIG. 14 can be made in a continuous process by means of the manufacturing stages illustrated in 15a, 15b, 15c and 15d.

According to FIG. 15a, a circular, cylindrical stylet with a diameter of about 0.30 mm is made first.

According to FIG. 15b, a pair of separate stylet segments, 540 mm long with a cross-sectional diameter of 19 mm, are then processed (ground down).

According to FIG. 15c, the parts of the stylet which still have a diameter of 0.30 mm are then worked until these parts have a non-circular cross-section with the dimensions 0.19 mm×0.30 mm. The finished stylet is then cut off at points S1—S1 and S2—S2 respectively.

According to FIG. 15d, the distal end of the stylet 70 made this way is equipped with a small end ball 20, and, finally, the distal end section 76 of the stylet is given its circular loop shape, as shown in FIG. 14.

Figure 16:
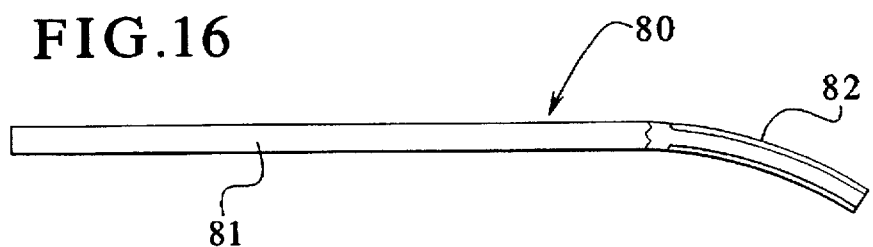
FIG. 16 is a side view, partly broken away, of a first version of a fourth embodiment of a stylet unit according to the invention.
Figure 17:
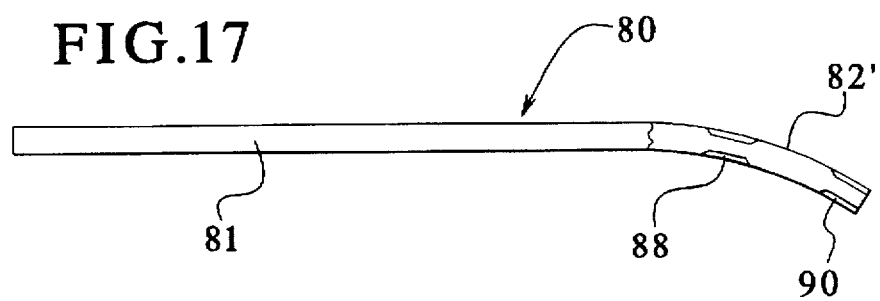
FIG. 17 is a side view, partly broken away, of a second version of the fourth embodiment of a stylet unit according to the invention.

FIGS. 16 and 17 respectively show different versions of a stylet sleeve 80 for a fourth embodiment of the inventive stylet unit. Each sleeve 80 has a section 81 with a circular cross-section. The sleeve 80 in FIG. 16 has a distal end section 82 with a non-circular cross-section which extends along the entire length of the distal end section 82. In the version of FIG. 17, the sleeve 80 has a distal end section 82' with a non-circular cross-section, the non-circular cross-section of the distal end section 82 being formed by spaced apart longitudinal sections 88 and 90.

Figure 18:
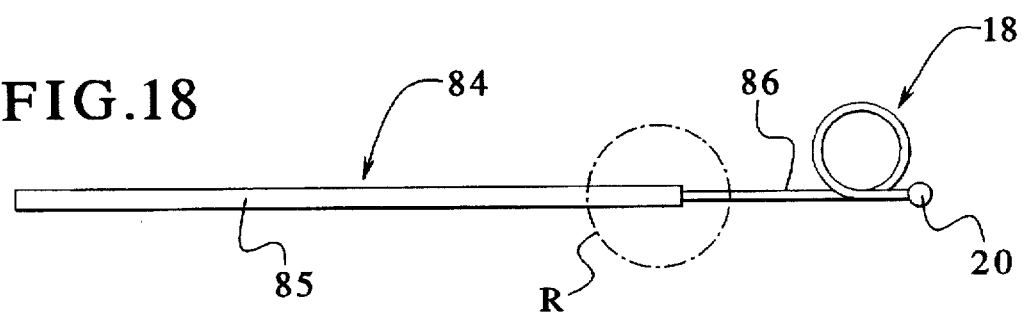
FIG. 18 is a side view of an inner stylet for use in either of the stylet sleeves of FIG. 16 or FIG. 17 in the fourth embodiment of a stylet unit according to the invention.

Each of the sleeves 80 shown in FIGS. 16 and 17 is for use with an inner stylet 84 as shown in FIG. 18. The inner stylet 84 of FIG. 18 has a section 85 with a circular cross-section, and a distal end section 86 with a non-circular cross-section. In this embodiment, the distal end section 86 of the inner stylet 84 is longer than the length of the respective distal end sections 82 and 82' of the two versions of the sleeve 80 shown in FIGS. 16 and 17. Preferably the distal end section 86 of the inner stylet 84 is at least two times longer than the length of the distal end sections 82 and 82'.

Figure 19:
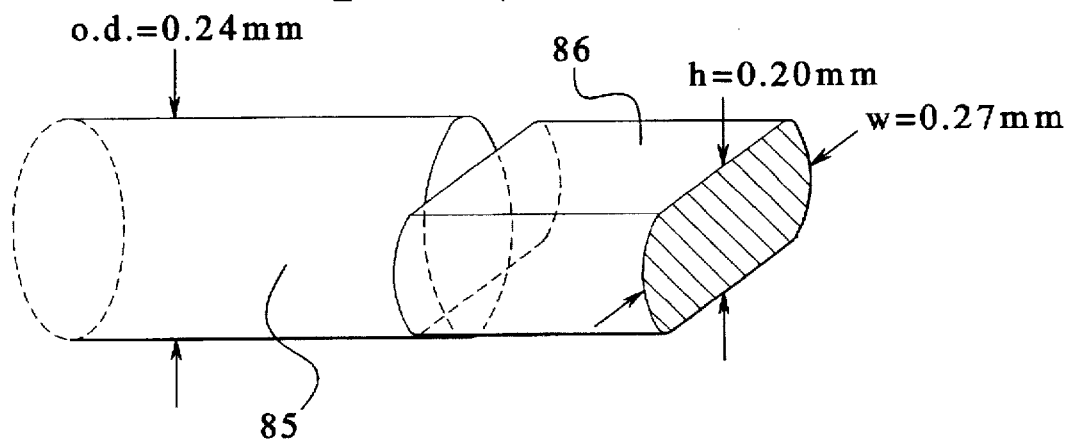
FIG. 19 is an enlarged view of the region R of FIG. 18.

The region R of FIG. 18 of the inner stylet 84 is shown enlarged in FIG. 19, wherein it can be seen that the section 85 having a circular cross-section has an outer diameter (o.d.) of 0.24 mm, and the non-circular distal end section 86 is, for example, generally rectangular in cross-section, with rounded sides, and has a height h of 0.20 mm and a width w of 0.27 mm.

Also in the fourth embodiment shown in FIGS. 16–19, the stylet sleeve 80 is pre-bent in a lateral direction, the section, such as the distal end section 82 or 82', having this pre-bend having a length which is approximately equal to the intended travel distance of the inner stylet 84 within the channel of the sleeve 80. The distal end section 86 of the inner stylet 84 has a length which is at least twice the length of the aforementioned travel distance.

Although modifications and changes may be suggested by those skilled in the art, it is the intention of the inventors to embody within the patent warranted hereon all changes and modifications as reasonably and properly come within the scope of their contribution to the art.

We claim as our invention:

1. A stylet unit for use with an elongate element having an internal longitudinal channel, said stylet unit being insertable into a channel of said elongate element to stiffen said elongate element and to bend a distal end section of said elongate element, said stylet unit comprising:

a flexible, tubular sleeve having a longitudinal channel therein;

a stylet insertable into said channel of said sleeve and having a distal stylet end section which is pre-bent in a direction in a plane;

said sleeve having at least one longitudinal sleeve section in which said channel has a non-circular cross-section, and having a distal sleeve end pre-bent in said plane in an opposite direction to said distal end stylet section; and said stylet having at least one longitudinal stylet section with a non-circular cross-section, the non-circular cross-section of said stylet section being matched to the non-circular cross-section of said sleeve section for preventing rotation of said stylet in said channel of said sleeve while allowing longitudinal movement of said stylet within said channel of said sleeve.

2. A stylet unit as claimed in claim 1 wherein said sleeve has a first longitudinal sleeve section having a circular cross-section, followed in the longitudinal direction by a second longitudinal section comprising said longitudinal sleeve section with a non-circular cross-section, and wherein said stylet has a non-circular cross-section along substantially an entire length of said stylet.

3. A stylet unit as claimed in claim 1 wherein said channel of said sleeve has a non-circular cross-section along substantially an entire length of said sleeve, and wherein said stylet has a first longitudinal section with said non-circular cross-section, followed in a longitudinal direction by a second longitudinal section having a circular cross-section, followed in said longitudinal direction by a third longitudinal section having said non-circular cross-section.

4. A stylet unit as claimed in claim 1 wherein each of said channel of said sleeve and said stylet have said non-circular cross-section along substantially their entire respective lengths for preventing rotation of said stylet in said channel of said sleeve along the entire length of said stylet.

5. A stylet unit as claimed in claim 1 wherein said distal sleeve end section has a curved length encompassing an angle less than 90°.

6. A stylet unit as claimed in claim 1 wherein said distal sleeve end section encompasses an angle less than 45°.

7. A stylet unit as claimed in claim 1 wherein said distal stylet end section is pre-bent with a substantially constant bending radius which is substantially less than the bending radius of said distal sleeve end section.

8. A stylet unit as claimed in claim 7 wherein said distal stylet end section has a curve length encompassing at least 360° so that said distal stylet end section forms a closed loop.

9. A stylet unit as claimed in claim 1 wherein said distal stylet end section has a curvature radius, a curve length and a flexural stiffness, and wherein said distal sleeve end section has a radius of curvature, a curve length and a flexural stiffness, the respective curvature radii, curve lengths and flexural stiffnesses of said distal stylet end section and said distal sleeve end section counteracting and cancelling each other when said stylet is completely encompassed in said sleeve so that said stylet unit has a straight configuration.

10. A stylet unit as claimed in claim 9 wherein said non-circular cross-section of said stylet is smaller than said non-circular cross-section of said channel so that a tolerance between said non-circular cross-sections of said stylet and said channel of at least 0.02 mm exists.

11. A stylet unit as claimed in claim 1 wherein said non-circular cross-section of said stylet is smaller than said non-circular cross-section of said channel so that a tolerance between said non-circular cross-sections of said stylet and said channel of at least 0.02 mm exists.

12. A stylet unit as claimed in claim 1 wherein the respective non-circular cross-section of said stylet section and said sleeve section are selected from the group consisting of concentric ovals, concentric ellipses and regular polygons having rounded corners.

13. A stylet unit as claimed in claim 1 wherein said distal stylet end section has a U-shape when deployed outside said sleeve.

14. A stylet unit as claimed in claim 1 wherein said distal stylet end section has a J-shape when deployed outside said sleeve.

15. A stylet unit as claimed in claim 1 wherein said longitudinal sleeve section is disposed at a distal end of said sleeve and wherein said longitudinal stylet section is disposed at a distal end of said stylet, and wherein said longitudinal stylet section has a length which is longer than a length of said longitudinal sleeve section.

16. A stylet unit as claimed in claim 15 wherein said length of said longitudinal stylet section is at least two times longer than the length of said longitudinal sleeve section.

17. A stylet unit as claimed in claim 15 wherein said longitudinal sleeve section has a non-circular cross-section along an entirety of its length.

18. A stylet unit as claimed in claim 15 wherein said longitudinal sleeve section comprises at least two spaced-apart longitudinal sleeve sub-sections, each of said longitudinal sleeve sub-sections having said non-circular cross-section.

19. A stylet unit as claimed in claim 11 wherein said longitudinal sleeve section is pre-bent in said plane along its entire length, said length of said longitudinal sleeve section being substantially equal to a distance of longitudinal movement of said stylet in said channel of said sleeve, and said longitudinal stylet section having a length which is at least twice as long as said distance of longitudinal movement.

20. A cable and stylet unit combination comprising:

a hollow electrode cable having a channel therein;

a stylet unit, insertable into said channel in said cable, said stylet unit comprising a stylet sleeve having an interior channel and a stylet movable in said interior channel, said channel of said stylet sleeve having at least a portion thereof with a non-circular cross-section and said stylet having at least a portion thereof with a non-circular cross-section for preventing rotation of said stylet in said channel of said stylet sleeve, and said stylet having a distal stylet end section which is pre-bent in a plane and said sleeve having a distal end;

a contact electrode disposed at a distal end of said cable; and said cable having a straight cable section and a distal end section forming a fish hook-like shape when said stylet unit is inserted as far as possible into said channel of said cable and said distal stylet end section has been deployed beyond said distal end of said sleeve in said channel of said cable, and said contact electrode being disposed substantially parallel to said straight section of said cable.

* * * * *